United States Patent [19]

Kaplan

[11] Patent Number: 5,282,861
[45] Date of Patent: Feb. 1, 1994

[54] OPEN CELL TANTALUM STRUCTURES FOR CANCELLOUS BONE IMPLANTS AND CELL AND TISSUE RECEPTORS

[75] Inventor: Richard B. Kaplan, Beverly Hills, Calif.

[73] Assignee: Ultramet, Pacoima, Calif.

[21] Appl. No.: 850,118

[22] Filed: Mar. 11, 1992

[51] Int. Cl.$^5$ ............ A61F 2/28; A61F 2/02; A61F 2/54; A01N 1/02
[52] U.S. Cl. .................... 623/16; 623/11; 623/66; 427/2
[58] Field of Search ............ 623/16, 11, 66; 427/2; 433/173, 201.1, 202.2, 206, 207

[56] References Cited

U.S. PATENT DOCUMENTS

| | | |
|---|---|---|
| 3,677,795 | 7/1972 | Bokros et al. ............ 623/2 |
| 3,992,725 | 11/1976 | Homsy ............ 623/11 |
| 4,392,828 | 7/1983 | Ehrnford ............ 433/201.1 X |
| 4,457,984 | 7/1984 | Otani et al. ............ 433/201.1 |
| 4,737,411 | 4/1988 | Graves, Jr. et al. ............ 623/16 X |
| 4,775,598 | 10/1988 | Jaeckel ............ 428/550 |
| 4,846,834 | 7/1989 | von Recum et al. ............ 427/2 X |
| 5,030,233 | 7/1991 | Ducheyne ............ 623/16 |
| 5,152,794 | 10/1992 | Davidson ............ 623/16 |

FOREIGN PATENT DOCUMENTS 2093701 9/1982 United Kingdom ............ 623/16

Primary Examiner—David Isabella
Assistant Examiner—Dinh X. Nguyen
Attorney, Agent, or Firm—Charles H. Schwartz; Ellsworth R. Roston

[57] ABSTRACT

A tantalum open cell structure is formed by chemical vapor deposition onto a reticulated carbon foam substrate. Tantalum has a long history of use as an implant material, in both bone and soft tissue. This lightweight, strong, porous structure, mimicking the microstructure of natural cancellous bone, acts as a matrix for the incorporation of bone, providing optimal permeability and a high surface area to encourage new bone ingrowth.

18 Claims, 4 Drawing Sheets

OPEN CELL TANTALUM STRUCTURES FOR CANCELLOUS BONE IMPLANTS AND CELL AND TISSUE RECEPTORS

BACKGROUND OF THE INVENTION

The need for a cancellous bone substitute and/or cell and tissue receptive material is significant. For example, cancellous autografts provide a porous framework within which revascularization occurs and against which new bone is layered, and also provide a population of osteoprogenitor cells and a complement of bone growth-inducing factors. Grafting, however, requires surgery to obtain the material, and a viable substitute is desirable. It is here that the concept of artificial biocompatible implants becomes of interest. Extensive studies over the last two decades have shown that to duplicate the success of cancellous grafts, an implant should serve as a porous framework. Indeed, early research demonstrated that an interconnected porous material is tolerated by the body, and encourages new bone growth, better than the same material in solid form.

The replacement of diseased, destroyed, or degenerative bone and tissues consumes time and financial resources from a large segment of the surgical community, in both medicine and dentistry. Clinical and scientific work is directed at facilitating regeneration of tissues in affected patients so that normal biomechanical and physiologic functions can resume. In some patients, full restoration of function with normal tissue is achievable, while in others, prostheses are biologically attached to restore function. The specialty science devoted to the study of substances utilized for implants in medicine and dentistry, biomaterials, is a young field that has taken tremendous strides in the last 20 years. Over the same period, dental implantology has evolved from early attempts by a few enthusiasts to a fully recognized branch of dentistry.

Although indispensable for survival, the body's natural defense mechanisms, by which materials identified as nonself are rejected, have been the nemesis of surgeons using prostheses or implantable devices. It is necessary to minimize the rejection mechanism as much as possible. Certain biomaterials have been identified as having apparently limited reactions to the body's defense mechanisms. These materials can be placed on a continuum that extends from relatively chemically reactive to completely nonreactive or passive. Generally, the more nonreactive the material is in vivo, the better the performance that can be expected.

Matching the requisite biomechanical requirements for an implant with the environment of surrounding tissues has been a formidable challenge. Significant progress was made in resolving this problem in the early 1970s, when the importance of porosity was first recognized. Later work showed that certain physical parameters of the porosity affect the type of tissue and the rate of ingrowth. The degree of interconnectivity and the nominal pore size were found to be critical factors in determining the success of an implant. Maximum interconnectivity, or the absence of "dead ends", was found to facilitate ingrowth. These studies showed that pore sizes less than 10 $\mu$m prevent ingrowth of cells; pore sizes of 15–50 $\mu$m encourage fibrovascular ingrowth; pore sizes to 50–150 $\mu$m result in osteoid formation; and pore sizes of greater than 150 $\mu$m facilitate the ingrowth of mineralized bone.

Bone ingrowth into the voids of a porous material provides ideal skeletal fixation for the permanent implants used for the replacement of bone segments lost due to any number of reasons, or in total joint prostheses. Biological compatibility, intimate contact with the surrounding bone, and adequate stability during the early period of bone ingrowth have been identified as important requirements, along with proper porosity. The optimal porous material should have good crack resistance, particularly under impact, and a compliance comparable to that of bone. The material should also make the manufacture of implants of precise dimensions easy, and permit the fabrication of either thick or thin coatings on load-bearing cores.

One prerequisite for successful ingrowth is that the implant be placed next to viable bone. In fact, the presence of bone within the implant has become presumptive evidence of osteoconductive properties: that is, the ability of bone to grow into a porous structure when the structure is placed next to bone. Initially, the cells that interface the implant convert to bone, then the front of regenerated bone progresses into the implant. This process is known as osseointegration, meaning the achievement of direct contact between living bone and implant.

The research, development, and manufacture of synthetic porous implants having the physical properties required to promote bone ingrowth have proved to be a major endeavor. Implants with porous surfaces of metallic, ceramic, polymeric, or composite materials have been studied extensively over the last two decades. A significant early advance in this area was made with the development of "replamineform" materials, so termed because they replicate actual life forms. These materials are based on the three-dimensional microstructure of certain marine invertebrates (best represented by corals and echinoids), which is uniform and completely permeable. The replamineform process utilizes the invertebrate microstructure as a template to make porous structures of other materials.

The most commonly used substance for porous biomaterials is calcium hydroxyapatite (HA), which is the largest chemical constituent of bone. Other nonmetallic materials frequently used in porous form for implants include the ceramics tricalcium phosphate (TCP), calcium aluminate, and alumina, carbon; various polymers, including polypropylene, polyethylene, and polyoxymethylene (delrin); and ceramic-reinforced or -coated polymers. Unfortunately, ceramics, while strong, are very brittle and often fracture readily under loading; and polymers, while possessing good ductility, are extremely weak. The very nature of these materials can restrict their clinical dental and orthopedic applications.

Metals, on the other hand, combine high strength and good ductility, making them attractive candidate materials for implants (and effectively the most suitable for load-bearing applications). Many dental and orthopedic implants contain metal, most often titanium or various alloys such as stainless steel or vitallium (cobalt-chromium-molybdenum). Ceramic-coated metals are also used, typically HA or TCP on titanium. Additionally, a large variety of metals are used internally in biomedical components such as wire, tubing, and radiopaque markers.

Many existing metallic biomaterials, however, do not easily lend themselves to fabrication into the porous structures that are most desirable for bone implants. These materials (e.g. stainless steel, cobalt-based alloys) exhibit the necessary properties and biocompatibility as long as only a smooth, bulk shape in a metallurgically perfect state is needed. The machining or other treatment needed to obtain a porous or surface-textured shape for interlocking with skeletal tissue can have a detrimental effect on the properties and biocompatibility, and can even result in material failure. For example, the hexagonal crystal structure of titanium makes it susceptible to cracks and fractures, as has been seen in the case of dental implants. Some porous metallic materials (e.g. flame- or plasma-sprayed titanium, porous sintered powder metallurgy materials) do not match the structure of cancellous bone sufficiently well to ensure successful ingrowth and integration. Also, most metals and alloys currently in use are subject to some degree of corrosion in a biological environment. Finally, the high densities of metals can make them undesirable from a weight standpoint.

SUMMARY OF THE INVENTION

New materials are enabling the design of innovative, and increasingly biocompatible, replacements for damaged human tissues. In the present invention, reticulated open cell carbon foam is infiltrated with tantalum by the chemical vapor deposition (CVD) process. It should be noted that niobium, which has similar chemical and mechanical properties to tantalum, may also be used as well as appropriate alloys of tantalum and niobium. For example, other metals such as niobium, hafnium and/or tungsten could be alloyed with the tantalum or hafnium and/or tungsten with niobium to change modulus and/or strength. Therefore, any reference to tantalum is not meant to be an exclusion of other metals.

The carbon foam is infiltrated by chemical vapor deposition (CVD). The resulting lightweight, strong, porous structure, mimicking the microstructure of natural cancellous bone, acts as a matrix for the incorporation of bone or reception of cells and tissue. The pores of the matrix are connected to one another to form continuous, uniform channels with no dead ends. This intricate network of interconnected pores provides optimal permeability and a high surface area to encourage cell and tissue ingrowth, vascularization, and deposition of new bone.

The result is a new biomaterial that, when placed next to bone or tissue, initially serves as a prosthesis and then functions as a scaffold for regeneration of normal tissues. The new biomaterial fulfills the need for an implant modality that has a precisely controllable shape and at the same time provides an optimal matrix for cell and bone ingrowth. Additionally, the physical and mechanical properties of the porous metal structure can be specifically tailored to the particular application at hand. This new implant offers the potential for use in alveolar ridge augmentation, periodontics, and orthognathic reconstruction. As an effective substitute for autografts, it will reduce the need for surgery to obtain those grafts. It is useful in orthopedic applications as well.

The present invention may also be used for tooth replacement because of the ability to induce tissue and bone growth even in the face of mildly infectious conditions. For example, an artificial tooth can be joined to an open cell tantalum stem and positioned in an appropriately sized hole in the jaw. The gum is allowed to rest against the artificial tooth and some of the stem to form a seal.

Tantalum was selected as the material of choice based on its good mechanical properties, excellent corrosion resistance, and demonstrated biocompatibility. Tantalum (atomic number 73, atomic weight 180.95, density 16.68 g/cm$^3$) is a transition element (periodic group VB), a highly refractory (melting point 2996° C.), strong, ductile metal with excellent oxidation and corrosion resistance. These properties led to its early investigation, in both animal and human experiments, as a potential human implant material. Early evidence of excellent tissue acceptance, combined with low corrosion, has led to the use of tantalum as a surgical implant material and its use in a variety of applications, including pacemaker electrodes, wire, foil and mesh for nerve repair, cranioplasty plates, contrast media for airwave radiographic studies, radiopaque markers for following bone growth, ligation clips, and more recently on an experimental basis in femoral endoprostheses.

The crystal structure of tantalum is body-centered cubic, giving it excellent ductility due to the six possible slip planes. It is so corrosion-resistant that it resists the attack of most chemical agents; tantalum pacemaker electrodes have exhibited excellent corrosion resistance both in vitro and in vivo. This inertness likely accounts for the good tissue compatibility of the base metal as well, whereas a noble metal such as gold, though considered corrosion-resistant, is not sufficiently biocompatible due to its catalytic surface.

Comparative studies have demonstrated that tantalum does not inhibit cell growth and indeed becomes tightly enveloped by new osseous tissue soon after implantation, whereas dental gold and cobalt-based alloys can inhibit cell growth and cause bone resorption. With tantalum, osseous ingrowth has been demonstrated right up to and into implants. Complete, strong, long-term osseointegration has been demonstrated with tantalum implants in both dental and orthopedic applications, under both unloaded and heavily loaded conditions, for implantation periods as long as eight to twelve years.

In addition, tantalum has an elastic modulus close to that of bone, much closer than any of the other high-strength metals and alloys commonly used for implants; this too may well contribute to the favorable reaction with bone. With its greater ductility, excellent corrosion resistance, good workability, and demonstrated biocompatibility, tantalum clearly can be regarded as an excellent alternative to the metals and alloys presently in use and under development for bone implants.

DESCRIPTION OF THE PREFERRED EMBODIMENT

Figure 1:
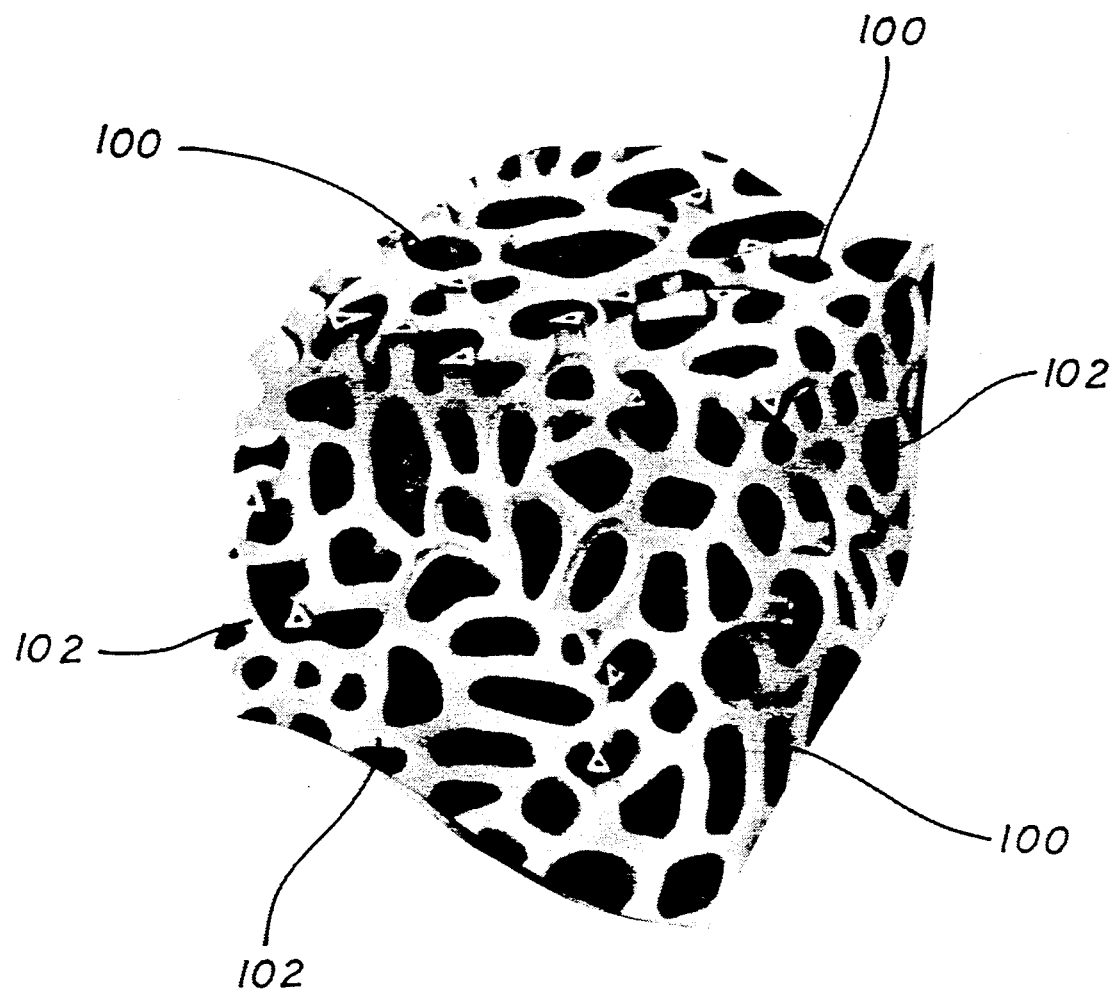
FIG. 1 is a perspective view of an open cell tantalum structure constructed in accordance with the present invention.

Cancellous, or spongy, bone is composed of a porous space-frame structure formed of open spaces defined by interconnected trabeculae, oriented along lines of principal stresses. At the microstructural level, the trabeculae are composed of layers of lamellar bone. Cancellous bone has anisotropic mechanical properties, i.e. different structural behavior along different orientations. Along the axis of the major channels, cancellous bone exhibits elastic behavior with sudden brittle failure at ultimate load in tension. When loaded with a tensile force whose line of action is skewed with respect to the channel axis of the bone, the stress-strain curve is parabolic with plastic deformation and greater energy absorption. It is therefore stiffer (has higher tensile and compressive moduli) but fails at a lower strain when loaded parallel to the predominant spicular direction than when loaded in other directions. These properties are important because they serve to absorb shock and distribute load in the vicinity of the articular surfaces of joints.

Any material to be used as a substitute for cancellous bone must therefore allow elastic deformation and load distribution. In addition, the material must not produce load concentrations, particularly if placed close to the underlying surface of articular cartilage, which might increase the local stresses on the articular surface and lead to wear and damage of the surface.

Cancellous bone demonstrates remodeling behavior according to Wolff's Law: that is, with the form being given, bone adapts to the loads applied to it. The converse is also true, and equally important: where loads are not applied, bone tends to resorb. An implant, then, must distribute stresses throughout its structure, the ingrowing bone, and the surrounding bone in order to avoid bone resorption and weakening caused by stress shielding.

The density of cancellous bone is 0.7 g/cm$^3$; its tensile modulus 0.2–0.5 GPa; tensile strength 10–12 MPa; and strain to failure 5–7%. Compared to cortical bone, cancellous bone is $\frac{1}{3}$–$\frac{1}{4}$ as dense (indicating its porous nature); 1/10–1/20 as stiff; and five times as ductile. The mechanical properties of the two types, though, actually represent a continuum, reflecting the behavior of a relatively uniform material (bone) modified by differences in density and structure.

Based on experiments with hydroxyapatite implants, ingrowth and maturation of new bone are more rapid from a cancellous bone region than from cortical bone, with the tissue-implant interface reaching peak shear strength in dogs in 8 weeks. The process may take longer in humans, with remodeling still possible up to 2 years postoperation. Inadequate device designs may produce continued stress shielding remodeling as long as 9–10 years postoperation.

Materials for osseous, or bone, implants must be rigid and stress-resistant, while avoiding self-concentration of stresses that result in stress shielding. Also, osseous implants should ideally reside in the bone without interfering with bone remineralization, the natural process by which the body replenishes bone. The implant should be able to be precisely shaped and placed for optimal interface and performance. Finally, non-resorption would be a beneficial quality for implants used in load-bearing applications, and/or those in which complete bone ingrowth is not possible.

Critical to the performance of a porous implant is the completeness of its interconnectivity. This is essential because constrictions between pores and isolated, deadend pockets can limit vascular support to ingrowing tissues; ischemia of the ingrowing bone cells results in failure of the implant. Incomplete vascularization or a reduction in the neovascularity also makes an implant vulnerable to bacterial colonization. Implants lacking completely interconnected porosity can also result in aberrant mineralization, stress shielding, low fatigue strength, and/or bulk displacement.

The open cell metal structure of the present invention offers highly interconnected, three-dimensional porosity that is uniform and consistent, a structure exceptionally similar to that of natural cancellous bone. In this way it is superior to other porous metallic implant materials, whose "porosity" is artificially produced via some form of surface treatment that does not result in a truly complete, open porosity. Examples of these methods include macroscopic porous coatings (e.g. metal microspheres or wires sintered or otherwise attached to a bulk surface); microscopic surface porosity (e.g. metal powder particles flame- or plasma-sprayed onto a bulk surface); and controlled surface undulations machined into a bulk surface.

Although certain porous ceramic materials do offer full porosity (e.g. the replamineform process for hydroxyapatite), they have properties inferior to metals as discussed previously. The open cell metal structure is osteoconductive, like other porous implants. Also, it is entirely biocompatible, based on the demonstrated biocompatibility of tantalum.

Allowing full mineralization is another extremely important property required of bone substitute materials. The highly organized process of bone formation is a complex process and is not fully understood. There are, however, certain prerequisites for mineralization such as adequate pore size, presumably larger than 150 $\mu$m with interconnect size in the range of 75 $\mu$m. A pore diameter of 200 $\mu$m corresponds to the average diameter of an osteon in human bone, while a pore diameter of 500 $\mu$m corresponds to remodeled cancellous bone. The open cell metal structures of the present invention can be fabricated to virtually any desired porosity and pore size, and can thus be matched perfectly with the surrounding natural bone in order to provide an optimal matrix for ingrowth and mineralization. Such close matching and flexibility are generally not available with other porous implant materials.

One concern with an implant must be the potential for stress shielding. According to Wolff's law, bone grows where it is needed (that is, where there is a stress). Stress on a bone normally stimulates that bone to grow. With an implant, it is primarily the stress/strain field created in the tissue around an implant that controls the interface remodeling. Stress shielding occurs when an overly stiff implant carries stresses that were previously applied to the bone in that area; it can result in inhibition of mineralization and maturation of the ingrowing bone, and/or the resorption of existing natural bone.

An implant, then, must distribute stresses throughout its structure, the ingrowing bone, and the surrounding bone in order to avoid bone resorption and weakening caused by stress shielding. Because metals are stronger than natural bone, this would seem to be a concern with a metallic implant in that the implant would itself focus and bear directly the majority of local loads and stresses that would ordinarily be placed on the bone, thus depriving both the existing and new bone of those forces which, in effect, help keep it at optimal strength.

The unique structure and properties of the open cell metal structures of the present invention, however, avoid this drawback altogether. The deposited thin films operate as an array within the porous metal body, contributing their exceptional mechanical properties to the structure at large. One result of this effect is that imposed loads are distributed throughout the body. In the case of a open cell metal bone implant, stresses are distributed into both the ingrowing new bone and the surrounding existing bone as well, thereby providing both the old and new bone with the normal, healthy forces they require.

In fact, with the ability to finely tailor the open cell metal structure's properties during the fabrication process, an implant can be designed to distribute stresses in a given direction(s), depending on the needs of the specific application at hand. The bonding of regenerated bone to the implant also helps to transfer stresses directly to the bone in and around the implant; this sharing of biofunction is a consequence of the composite nature of the implant/bone structure. The advantage of these metal structures over other porous implant materials is especially strong in this area. Ceramics lack sufficient mechanical properties to begin with, and no current implant material, either ceramic or metallic, possesses the unique properties of the metal structure as described here.

In the present invention, useful lightweight refractory structures are made by the chemical vapor deposition (CVD) of a small amount of metallic material such as tantalum or niobium (or combination of these materials with other materials to form alloys) into a reticulated (porous) vitreous carbon foam. The density of the resultant body is purposely maintained at substantially below full density, resulting in a structure with extremely favorable properties. The basic approach involves the use of a low-density carbon foam, which is infiltrated with the desired material by CVD to provide uniform thin films on all ligaments. These thin films provide exceptional strength and stiffness to the ligaments, with the expenditure of very little weight. Thin CVD films can provide much higher mechanical properties than can bulk materials. Such quasi-honeycomb materials have remarkably high specific strength and stiffness.

This process does not endeavor to densify the body fully, although it is possible to do so, and useful parts can be so fabricated. In the present invention, only thin films are deposited on the interior surfaces of the vitreous carbon foam, taking advantage of the apparent unusual mechanical properties of the thin films which, when operating as an array in the body as a whole, produce unusual properties for the entire body. Using a porous carbon with extremely high porosity and small pore size takes advantage not only of the properties of thin films, but of short beams as well.

It is important to note that the structural integrity of the fabricated structure is provided by the deposited thin films themselves, rather than by the carbon foam substrate. These films have much higher moduli of elasticity than do the thin sections of vitreous carbon in the foam substrate. Because the deposited films are so thin and short, they show great strength, not unlike the high strength experienced in very fine fibers or filaments. Their support of the mechanical load ensures that failure does not occur in the carbon.

Figure 2:
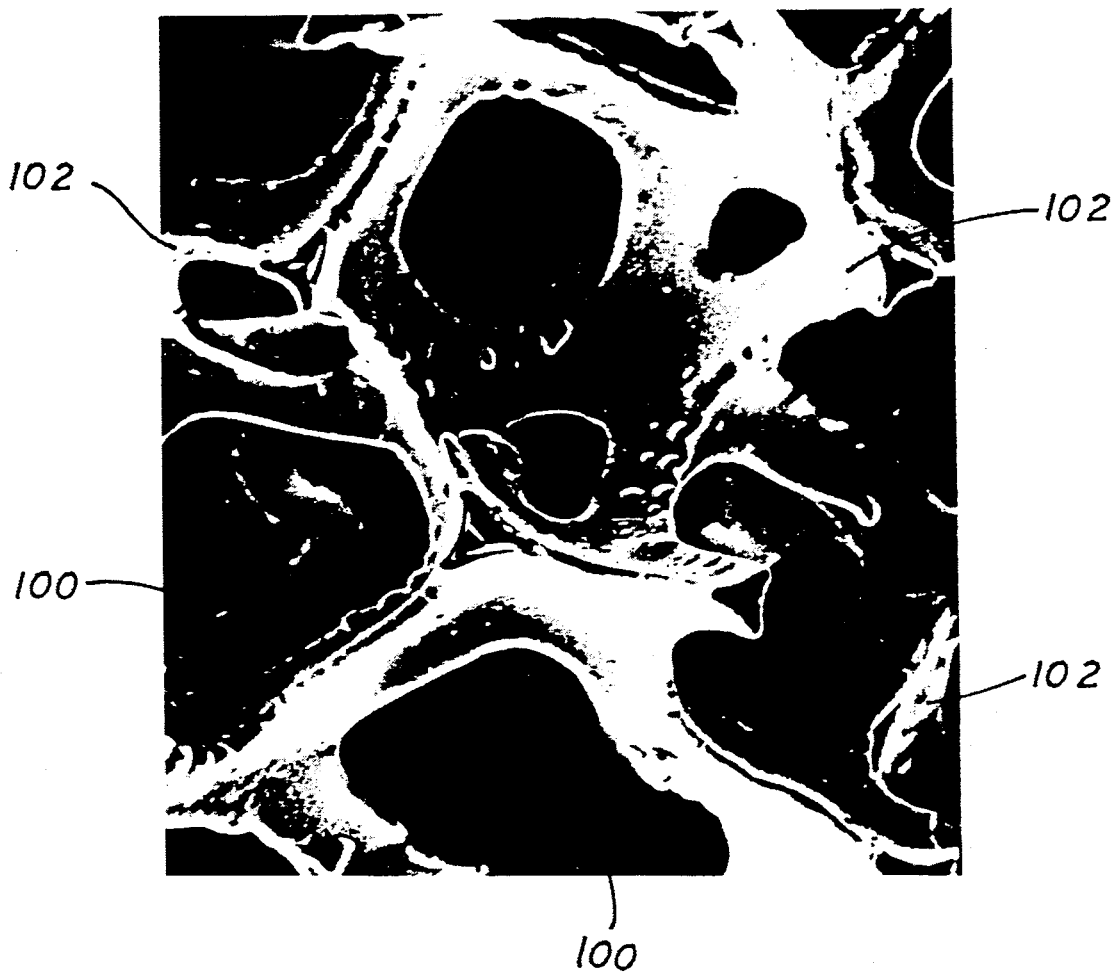
FIG. 2 is an enlarged view of the surface of the tantalum structure of FIG. 1.
Figure 3:
FIG. 3 is a detailed view of small sections of the material of FIGS. 1 and 2.

The open cell metal structures of the present invention are fabricated using the tantalum metal film and carbon substrate combination, with the film deposited by CVD, to form the structure shown in FIG. 1 which mimics bone closely in having open spaces 100 interconnected by ligaments 102. With the variables available in both the materials and the fabrication process, it is possible to obtain the simultaneous optimization of multiple properties (e.g. strength, stiffness, density, weight) for the given application of substitution for bone. FIGS. 2 and 3 are scanning electron photomicrographs showing the ligamental structure of the metal-infiltrated reticulated carbon foam and an individual coated ligament in cross-section, respectively. In FIG. 3 it can be seen that each ligament is formed by a carbon core 104 covered by a thin film 106 of metal such as tantalum, niobium or alloys of each.

Another major advantage of the open cell metal structure of the present invention is that it is readily shapeable to nearly any configuration, simple or complex, simply by shaping the raw carbon substrate prior to metal infiltration. This facilitates exact contouring of the implant for the specific application and location; precise placement is enhanced and bulk displacement is prevented. Additionally, it appears that any final shaping/trimming needed at surgery can be accomplished on the final device using conventional dental or orthopedic equipment available at the time of surgery.

The optimal conditions for fracture healing and long-term stability can be met if an implant can be designed allowing for motionlessness along all the interfaces necessary for a stable anchorage, thereby excluding (to the greatest extent possible) all outside influences on the remodeling process and allowing the local stress/strain field to control.

Following implantation and initial tissue ingrowth, the metal foam device stays where it is placed without retention aids, a reflection of precise contouring and the rapid ingrowth of fibrovascular tissue to prevent dislodgement. The binding between bone and implant stabilizes the implant and prevents loosening. These implants thus will not need to be held in place by other means (e.g. sutures or cement); rather, the growth of a natural bone-to-bone seal is encouraged by the nature of the implant itself. Tissue ingrowth would not be a contributing factor to device retention for a period following implantation, however, until a substantial amount of ingrowth had occurred.

The ability to precisely contour the device, along with its "Velcro-like" surface texture that provides multipoint contact with the surrounding tissue, is of some aid in retention, although mechanical aids may still be necessary at first. If needed, sutures would seem to lend themselves well to use with the open cell metal structure, while compatibility studies with cement and other bonding aids have been identified as an area of future investigation.

Broad-scale clinical adoption of bone grafting onto the alveolar ridge and for certain orthognathic reconstruction has been hindered by the well-established problem of resorption. Hydroxyapatite implants undergo some degree of chemical dissolution, often limiting their effectiveness as porous bone implants. Studies have shown that too-rapid degradation can inhibit the ongoing regeneration of bone throughout the implant. A permanent, nonresorbing implant can afford long-term maintenance of the augmentation and thereby overcome the resorption problem. However, permanent implants can be vulnerable to infection, loosening, or extrusion due to a lack of chemical or biomechanical compatibility and/or incomplete cellular ingrowth.

An open cell metal implant, being metallic, will undergo no resorption, and its anticipated complete biocompatibility and osteoconductivity render such concerns moot. Non-resorption is also beneficial in load-carrying applications where complete bone ingrowth cannot be achieved; the continued presence of the tantalum structures, with their superior mechanical properties, is beneficial in such circumstances.

The advantages of the open cell metal structure for bone implants are summarized as follows:
a. lightweight, low-density
b. very strong
c. biocompatible
d. high interconnected, uniform, three-dimensional porosity with high void fraction; structure similar to natural cancellous bone, with resultant osteoconductivity
e. fabricable to virtually any desired porosity/pore size
f. excellent mechanical properties
g. imposed loads distributed throughout the structure and into both the ingrowing new bone and the surrounding existing bone as well, avoiding stress shielding
h. readily shapeable to most desired configurations
i. non-resorbing
j. nearly all physical and mechanical properties can be tailored for a specific application, due to the number of fabrication variables available to be manipulated and the versatility of the CVD process.

Figure 4:
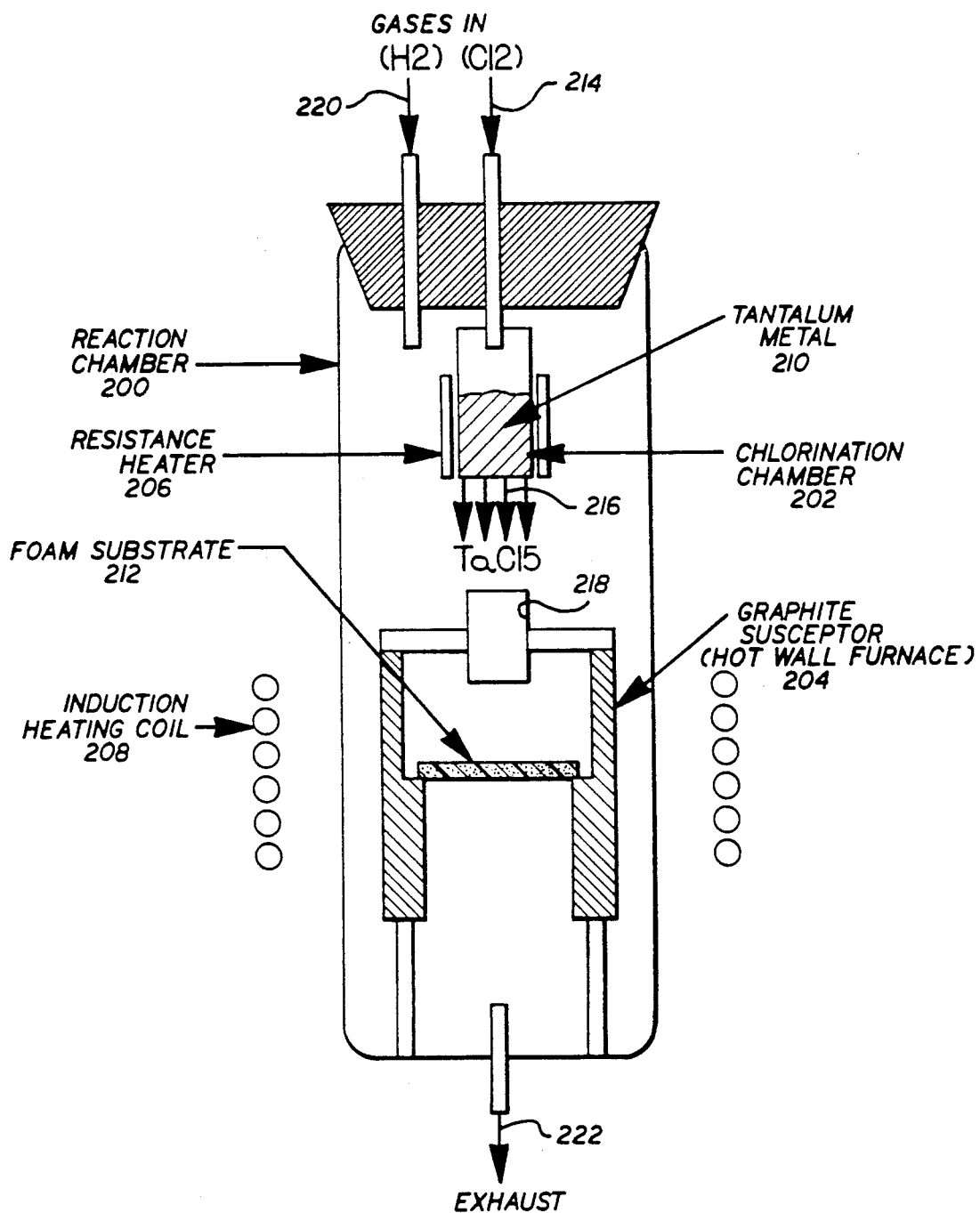
FIG. 4 is illustrative of one method of making the tantalum structure of the present invention.

FIG. 4 illustrates an apparatus for depositing the metal, such as tantalum, on the carbon foam substrate. A reaction chamber 200 encloses a chlorination chamber 202 and a hot wall furnace 204. A resistance heater 206 surrounds the chlorination chamber 202 and an induction heating coil 208 surrounds the reaction chamber 200 to heat the hot wall furnace 204.

Tantalum metal 210 is located within the chlorination chamber 202 and a carbon foam substrate 212 is positioned within the hot wall furnace. Chlorine gas, as shown by arrow 214 is injected into the chlorination chamber 202 to react with the tantalum to form tantalum chloride, as shown by arrows 216. The tantalum chloride mixes with Hydrogen injected into the chamber 200 as shown by arrow 220 and then passes through an opening 218 in the hot wall furnace 204. The mixture is heated within the hot wall furnace of a temperature of approximately 1100° C. to produce the following reacting surface $TaCl_5 + 5/2\ H_2 \rightarrow Ta + 5\ HCl$. The surface reaction deposits the tantalum on the carbon foam substrate 212 to produce the uniform thin film over the individual ligaments of the substrate as shown in FIG. 3. The Hydrogen Chloride is then exhausted as shown by arrow 222.

It should be appreciated that although the substrate 212 has been indicated to be carbon, other carboneous materials, such as graphite, may be used. In addition, other open cell materials, such as high temperature ceramics, may also be used. Also, other layers may be deposited on the substrate, such as intermediate layers to provide additional strength. Other aspects of the invention could be the incorporation of a core of solid material, such as tantalum or niobium or alloys of each, with the porous substrate fitted around the solid core and with the subsequent deposition of metal not only covering the substrate but also locking the porous substrate to the solid core.

Although the present invention has been described with reference to a particular method of manufacture, such as chemical vapor deposition, other methods of manufacture may be used. For example, electrodeposition by fused salt electrolysis may be used to deposit the tantalum on the carbon substrate.

The invention, therefore, is only to be limited to the appended claims.

I claim:

1. A cancellous bone substitute and cell and tissue reception material, including,
   a reticulated open cell substrate formed of a lightweight substantially rigid foam carbonaceous material having open spaces defined by an interconnecting network wherein said foam material has interconencted continuous channels, and
   a thin film of metallic material deposited onto the reticulated open cell substrate and covering substantially all of the interconnecting network to form a composite porous biomaterial creating a porous microstructure similar to that of natural cancellous bone.

2. The bone substitute material of claim 1 wherein the carbonaceous material is carbon.

3. The bone substitute material of claim 1 wherein the carbonaceous material is graphite.

4. A cancellous bone substitute and cell and tissue receptive material, including,
   a reticulated open cell substrate formed of a lightweight substantially rigid foam ceramic materal having open spaces defined by an interconnecting network wherein said foam material has interconnected continuous channels, and
   a thin film of metallic material deposited onto the reticulated open cell substrate and covering substantially all of the interconnecting network to form a composite porous biomaterial creating a porous microstructure similar to that of natural cancellous bone.

5. The bone substitute material of claim 4 wherein the ceramic is refractory.

6. A composite material useful as a bone substitute for bone implants and cell and tissue reception, the structure of which is characterized by a non-metallic open cell substantially rigid foam carbonaceous substrate formed by an interconnected network having interconnected continuous channels to create a porous microstructure similar to that of cancellous bone and a metallic film substantially covering the interconnected network.

7. The composite material of claim 6 wherein the carbonaceous material is carbon.

8. The composite material of claim 6 wherein the carbonaceous material is graphite.

9. A cancellous bone substitute and cell and tissue receptive material, including,
   a reticulated open cell substrate formed of a lightweight substantially rigid foam material having open spaces defined by an interconnecting network wherein said foam material has interconnected continuous channels, and
   a thin film of tantalum material deposited onto the reticulated open cell substrate and covering substantially all of the interconnecting network to form a composite porous biomaterial creating a porous microstructure similar to that of natural cancellous bone.

10. A cancellous bone substitute and cell and tissue receptive material, including,
    a reticulated open cell substrate formed of a lightweight substantially rigid foam material having open spaced defined by an interconnecting network wherein said foam material has interconnected continuous channels, and
    a thin film of tantalum alloy material deposited onto the reticulated open cell substrate and covering substantially all of the interconnecting network to form a composite porous biomaterial creating a porous microstructure similar to that of natural cancellous bone.

11. A cancellous bone substitute and cell and tissue receptive material, including,
   a reticulated open cell substrate formed of a lightweight substantially rigid foam material having open spaces defined by an interconnecting network wherein said foam material has interconnected continuous channels, and
   a thin film of niobium material deposited onto the reticulated open cell substrate and covering substantially all of the interconnecting network to form a composite porous biomaterial creating a porous microstructure similar to that of natural cancellous bone.

12. A cancellous bone substitute and cell and tissue receptive material, including,
   a reticulated open cell substrate formed of a lightweight substantially rigid foam material having open spaced defined by an interconnecting network wherein said foam material has interconnected continuous channels, and
   a thin film of niobium alloy material deposited onto the reticulated open cell substrate and covering substantially all of the interconnecting network to form a composite porous biomaterial creating a porous microstructure similar to that of natural cancellous bone.

13. A composite material useful as a bone substitute for bone implants and cell and tissue reception, the structure of which is characterized by a non-metallic open cell substantially rigid foam ceramic substrate formed by an interconnected network having interconnected continuous channels to create a porous microstructure similar to that of cancellous bone and a metallic film substantially covering the interconnected network.

14. The composite material of claim 13 wherein the ceramic is refractory.

15. A composite material useful as a bone substitute for bone implants and cell and tissue reception, the structure of which is characterized by a non-metallic open cell substantially rigid foam substrate formed by an interconnected network having interconnected continuous channels to create a porous microstructure similar to that of cancellous bone and a tantalum film substantially covering the interconnected network.

16. A composite material useful as a bone substitute for bone implants and cell and tissue reception, the structure of which is characterized by a non-metallic open cell substantially rigid foam substrate formed by an interconnected network having interconnected continuous channels to create a porous microstructure similar to that of cancellous bone and a tantalum alloy film substantially covering the interconnected network.

17. A composite material useful as a bone substitute for bone implants and cell and tissue reception, the structure of which is characterized by a non-metallic open cell substantially rigid foam substrate formed by an interconnected network having interconnected continuous channels to create a porous microstructure similar to that of cancellous bone and a niobium film substantially covering the interconnected network.

18. A composite material useful as a bone substitute for bone implants and cell and tissue reception, the structure of which is characterized by a non-metallic open cell substantially rigid foam substrated formed by an interconnected network having interconnected continuous channels to create a porous microstructure similar to that of cancellous bone and a niobium alloy film substantially covering the interconnected network.

* * * * *